(12) United States Patent
Hu et al.

(10) Patent No.: US 10,275,884 B2
(45) Date of Patent: Apr. 30, 2019

(54) METHODS AND SYSTEMS FOR IDENTIFYING ANATOMICAL LANDMARKS IN IMAGE DATA

(71) Applicants: Smith & Nephew, Inc., Memphis, TN (US); Smith & Nephew Pte. Limited, Tolaram (SG); Smith & Nephew Orthopaedics AG, Baar (CH)

(72) Inventors: Yangqiu Hu, Lewis Center, OH (US); Angela Mines, Arlington, TN (US); Nathaniel Lenz, Germantown, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

(21) Appl. No.: 16/152,211

(22) Filed: Oct. 4, 2018

(65) Prior Publication Data
US 2019/0035081 A1   Jan. 31, 2019

Related U.S. Application Data

(63) Continuation of application No. 15/124,988, filed as application No. PCT/US2015/019615 on Mar. 10, 2015.
(Continued)

(51) Int. Cl.
*G06T 7/60* (2017.01)
*G06T 19/20* (2011.01)
(Continued)

(52) U.S. Cl.
CPC .......... *G06T 7/0016* (2013.01); *A61B 5/055* (2013.01); *A61B 5/4504* (2013.01);
(Continued)

(58) Field of Classification Search
None
See application file for complete search history.

(56) References Cited

U.S. PATENT DOCUMENTS 5,408,409 A * 4/1995 Glassman .............. B25J 9/1679
600/407
6,205,411 B1   3/2001 DiGioia, III et al.
(Continued)

FOREIGN PATENT DOCUMENTS

EP   2371291 A1   10/2011
EP   3116389 A4   11/2017
(Continued)

OTHER PUBLICATIONS

Chao et al. "Simulation and Animation of Musculosketal Joint System" (Nov. 1, 1993) J. Biomechanical Engineering 115(4B): 562-568.
Delp et al. "An Interactive Graphics-Based Model of the Lower Extremity to Study Orthopaedic Surgical Procedures" (Aug. 1990) IEE Transactions on Biomedical Engineering 37(8): 757-767.
DiGioia et al. "An Integrated Approach to Medical Robotics and Computer Assisted Surgery in Orthopaedics" (1995) Carnegie Mellon University 106-111.
(Continued)

*Primary Examiner* — Nancy Bitar
(74) *Attorney, Agent, or Firm* — Pepper Hamilton LLP

(57) ABSTRACT

Systems, devices, and methods are described for locating and identifying anatomical landmarks, such as ligament attachment points, in image data. These systems, devices, and methods may provide an oblique plane that contains an anatomical landmark such as a ligament attachment point to the tibia. For example, the position at which the anterior cruciate ligament (ACL), medial collateral ligament (MCL) posterior cruciate ligament (PCL), or patellar tendon attaches to the tibia may be identified. The systems, devices, and methods allow for tracing of an anatomical landmark to generate a 3-D marking on a 3-D surface model of a patient's bone. The attachment points may be useful landmarks for patient-matched instrumentation.

20 Claims, 10 Drawing Sheets

Related U.S. Application Data

(60) Provisional application No. 61/950,756, filed on Mar. 10, 2014.

(51) Int. Cl.

| | |
|---|---|
| *G06T 7/00* | (2017.01) |
| *G06T 19/00* | (2011.01) |
| *G06T 7/73* | (2017.01) |
| *A61B 5/055* | (2006.01) |
| *A61B 5/00* | (2006.01) |
| *G06T 17/00* | (2006.01) |
| *A61B 6/03* | (2006.01) |
| *A61B 6/00* | (2006.01) |
| *A61B 8/08* | (2006.01) |
| *A61B 8/00* | (2006.01) |

(52) U.S. Cl.
CPC .......... *A61B 5/4523* (2013.01); *A61B 5/4533* (2013.01); *A61B 5/4887* (2013.01); *A61B 5/742* (2013.01); *A61B 6/032* (2013.01); *A61B 6/466* (2013.01); *A61B 6/50* (2013.01); *A61B 6/505* (2013.01); *A61B 6/5217* (2013.01); *A61B 6/5223* (2013.01); *A61B 8/0875* (2013.01); *A61B 8/466* (2013.01); *A61B 8/483* (2013.01); *G06T 7/60* (2013.01); *G06T 7/75* (2017.01); *G06T 17/00* (2013.01); *G06T 19/00* (2013.01); *G06T 19/20* (2013.01); *A61B 5/4528* (2013.01); *A61B 8/085* (2013.01); *A61B 8/5223* (2013.01); *A61B 2576/00* (2013.01); *G06T 2207/10* (2013.01); *G06T 2207/30008* (2013.01); *G06T 2207/30204* (2013.01); *G06T 2210/32* (2013.01); *G06T 2219/004* (2013.01); *G06T 2219/008* (2013.01); *G06T 2219/028* (2013.01)

(56) References Cited

U.S. PATENT DOCUMENTS

| | | | |
|---|---|---|---|
| 7,211,046 | B2 | 5/2007 | Deller |
| 7,797,030 | B2 | 9/2010 | Lahm |
| 2004/0122309 | A1 | 6/2004 | Deller et al. |
| 2005/0148850 | A1 | 7/2005 | Lahm et al. |
| 2007/0253610 | A1* | 11/2007 | Pieper ............... G06T 7/62 382/128 |
| 2011/0255764 | A1* | 10/2011 | Lin .................. G06T 19/00 382/131 |

FOREIGN PATENT DOCUMENTS

| | | |
|---|---|---|
| WO | 2006126150 A2 | 11/2006 |
| WO | 2015138397 A1 | 9/2015 |

OTHER PUBLICATIONS

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

Dillman et al. "Haptic Devices in Medical Applications" (Jun. 23, 1999) Institute for Process Control and Robotics, 1st International Workshop, Paris, France, pp. 12-22.

Drape et al: "3 CT scans and arthro-CT scans", Bailliere's Best Practice and Research. Clinical Reumato, Bailliere Tindall, London, GB, vol. 10, No. 4, Nov. 1, 1996 (Nov. 1, 1996), pp. 615-634, XP005814715, ISSN: 1521-6942, DOI: 10.1016/S1521-6942(05)80004-X.

Freysinger et al. "A Passive-Marker-Based Optical System for Computer-Aided Surgery in Otorhinolaryngology: Development and First Clinical Experiences" (Feb. 2002) The Laryngoscope 112(2):409.

Harris et al. "Experiences with Robotic Systems for Knee Surgery" (Mar. 19-22, 1997) Springer-Verlag, London, UK 757-766.

Hill Nathan B et al: "Magnetic resonance imaging of injury to the medial collateral ligament of the elbow: A cadaver model", Journal of Shoulder and Elbow Surgery, vol. 9, No. 5, Jan. 1, 2000 (Jan. 1, 2000), pp. 418-422, XP028775608, ISSN: 1058-2746, DOI: 10.1067/MSE.2000.107392.

International Search Report for related PCT/US2015/019615 dated May 29, 2015.

Luyun Chen et al: "Cardinal and deep uterosacral ligament lines of action: MRI based 3D technique development and preliminary findings in normal women", International Urogynecology Journal ; Including Pelvic Floor Dysfunction, Springer-Verlag, LO, vol. 24, No. 1, May 23, 2012 (May 23, 2012), pp. 37-45, XP035158139, ISSN: 1433-3023, DOI: 10.1007/S00192-012-1801-4.

O'Toole III et al. "Towards More Capable and Less Invasive Robotic Surgery in Orthopaedics" (1995) Computer Vision, Virtual Reality and Robotics in Medicine 905: 123-130.

Supplementary European search report for related EP 15761756 dated Oct. 5, 2017.

Taylor et al. "An Image-Directed Robotic System for Precise Orthopaedic Surgery" (Jun. 1994) IEE Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

Wilson D L et al: "Estimation of Tendon Moment Arms From Three-Dimensional Magnetic Resonance Images", Annals of Biomedical Enginee, Springer US, New York, vol. 27, No. 2, Mar. 1, 1999 (Mar. 1, 1999), pp. 247-256, XP008060726, ISSN: 0090-6964, DOI: 10.1114/1.180.

Written Opinion for related PCT/US2015/019615 dated May 29, 2015.

* cited by examiner

METHODS AND SYSTEMS FOR IDENTIFYING ANATOMICAL LANDMARKS IN IMAGE DATA

CROSS REFERENCE TO RELATED APPLICATIONS

This application is a continuation application of U.S. patent application Ser. No. 15/124,988, filed on Sep. 9, 2016, and titled "Methods and Systems for Identifying Anatomical Landmarks in Image Data," which is a U.S. national stage filing under 35 U.S.C. § 371 of International Application No. PCT/US2015/019615, filed on Mar. 10, 2015, which claims the benefit of U.S. Provisional Application No. 61/950,756, filed on Mar. 10, 2014, each of which is hereby incorporated herein by reference in its entirety.

BACKGROUND

Accurate location of anatomical landmarks, such as ligament attachment points, in patient image data is critical to the overall outcome of patient-matched instrumentation techniques. Ligament attachment points can be used to facilitate consistent placement of implants on a patient's bone and may offer surgeons a reliable frame of reference for properly orienting implants. However, the location of ligament attachment points may not be known by a surgeon before a surgical operation and may need to be assessed intraoperatively. Noninvasive imaging techniques, such as MRI scans and CT scans, allow image data representing a patient's joint to be collected in advance of a surgical procedure. However, it can be difficult to use the raw image data collected from preoperative imaging to provide a surgeon with accurate preoperative information about the location of ligament attachment points.

The location of anatomical landmarks in such image data is evaluated using 2-D slices within the orthogonal planes of a 3-D volume (e.g., coronal, sagittal, and axial planes). This approach provides suboptimal visualization of ligament attachment points that are not adequately depicted in any of these planes. As a result, identifying such attachment points (e.g. attachments points on epicondyles) is a time-consuming process and suffers from high inter-operator variability. Therefore, to facilitate accurate preoperative location of ligament attachment points, there is a need for improved visualization of ligament attachment points.

SUMMARY

Disclosed herein are systems, devices, and methods for locating anatomical landmarks, such as ligament attachment points, in image data. In certain implementations, the systems, devices, and methods include receiving image data, identifying a base oblique plane that is oblique to the orthogonal planes in the image data, generating an adjusted set of orthogonal planes based on the base oblique plane, and generating reformatted images sampled along the adjusted set of orthogonal planes. These systems, devices, and methods may provide an oblique plane that more adequately contains an anatomical landmark such as a ligament attachment point to the tibia. In particular, the method may be used to identify where the anterior cruciate ligament (ACL), medial collateral ligament (MCL) posterior cruciate ligament (PCL), or patellar tendon attaches to the tibia. The systems, devices, and methods may allow tracing of an anatomical landmark in the reformatted image to generate a 3-D marking on a 3-D surface model of a patient's bone. The attachment points may be useful landmarks for patient-matched instrumentation. The systems, devices, and methods may also facilitate surgical planning. For example, the ligament locations may be used for preoperative planning and for designing patient-matched cutting blocks.

According to one aspect, a method for locating anatomical landmarks in image data includes receiving, at a processor, image data representative of a patient's joint, identifying an oblique plane intersecting a soft tissue represented in the image data and normal to a longitudinal axis of the soft tissue, identifying, with the processor, a set of planes parallel or orthogonal to the oblique plane, generating, with the processor, a set of reformatted images, from the image data, sampled along the set of planes, tracing a feature of the soft tissue in the set of reformatted images, and generating, with the processor, a 3-D marking representing the traced feature on a 3-D model. In some implementations, the image data is raw image data. Tracing the feature may include tracing the feature in two or more reformatted images parallel to the oblique plane. Tracing the feature may include advancing through parallel reformatted images selected from the set of reformatted images. Tracing the feature may include displaying a first reformatted image on a screen and displaying a second reformatted image on the screen, wherein the second reformatted image is parallel to and offset from the first reformatted image. Tracing the feature may include outlining a cross-section of the feature in a reformatted image from the set of reformatted images. Tracing the feature may include storing data representing the tracing in a matrix.

In certain implementations, generating the set of reformatted images includes rotating the image data. Identifying the oblique plane may include identifying a first point and a second point along the longitudinal axis of the soft tissue, evaluating, with the processor, a line defined by the first and second points, and evaluating, with the processor, a plane normal to the line. The first point may be located about where the soft tissue attaches to a patient's bone. The second point may be located at about the center of the soft tissue. The first point may be located at about the start of the soft tissue and the second point may be located at about the end of the soft tissue. The longitudinal axis of the soft tissue may be curved.

In certain implementations, identifying the oblique plane includes drawing a curve substantially parallel to the longitudinal axis of the tissue, and evaluating, with the processor, an oblique plane normal to the curve at the point where the oblique plane intersects the curve. In certain implementations, a plurality of reformatted images is generated, each reformatted image being normal to the curve at the point where each reformatted image intersects the curve. Generating the 3-D marking may include generating a 3-D surface model from the matrix. In certain implementations, the method further includes smoothing the 3-D marking. The 3-D model may be a model of a patient's bone. The 3-D model may be a model of a patient's tibia. The 3-D model may be displayed with the image data to orient a user.

In certain implementations, generating the set of reformatted images includes identifying, with the processor, four corners of the oblique plane, generating, with the processor, texture coordinates using the corner locations, and interpolating, with the processor, pixel intensities for the texture coordinates using the image data. The soft tissue may be an ACL, a MCL, a PCL, or a patellar tendon of a patient.

According to one aspect, a system for locating anatomical landmarks in image data includes means for receiving image data representative of a patient's joint, means for identifying an oblique plane intersecting a soft tissue represented in the image data and normal to a longitudinal axis of the soft tissue, means for identifying a set of planes parallel or orthogonal to the oblique plane, means for generating a set of reformatted images, from the image data, sampled along the set of planes, means for tracing a feature of the soft tissue in the set of reformatted images, and means for generating a 3-D marking representing the traced feature on a 3-D model. In some implementations, the image data is raw image data. The means for tracing the feature may include means for tracing the feature in two or more reformatted images parallel to the oblique plane. The means for tracing the feature may include means for advancing through parallel reformatted images selected from the set of reformatted images.

In certain implementations, the means for tracing the feature includes means for outlining a cross-section of the feature in a reformatted image from the set of reformatted images. The means for tracing the feature may include means for storing data representing the tracing in a matrix. The means for generating the set of reformatted images may include means for rotating the image data. The means for identifying the oblique plane may include means for identifying a first point and a second point along the longitudinal axis of the soft tissue, means for evaluating a line defined by the first and second points, and means for evaluating a plane normal to the line. The first point may be located about where the soft tissue attaches to a patient's bone. The second point may be located at about the center of the soft tissue. The first point may be located at about the start of the soft tissue and the second point may be located at about the end of the soft tissue. The longitudinal axis of the soft tissue may be curved.

In certain implementations, the means for identifying the oblique plane includes means for drawing a curve substantially parallel to the longitudinal axis of the tissue, and means for evaluating an oblique plane normal to the curve at the point where the oblique plane intersects the curve. In certain implementations a plurality of reformatted images is generated, each reformatted image being normal to the curve at the point where each reformatted image intersects the curve. The means for generating the 3-D marking may include means for generating a 3-D surface model from the matrix. In certain implementations, the system further includes means for smoothing the 3-D marking.

In certain implementations, the 3-D model is a model of a patient's bone. The 3-D model may be a model of a patient's tibia. The 3-D model may be displayed with the image data to orient a user. In certain implementations, the means for generating the set of reformatted images includes means for computing four corners of the oblique plane, means for generating texture coordinates using the corner locations, and means for interpolating pixel intensities for the texture coordinates using the image data. In certain implementations the soft tissue is an ACL, a MCL, a PCL, or a patellar tendon of a patient.

According to one aspect, a method for locating anatomical landmarks in image data, includes receiving, at a processor, image data representative of a patient's joint, identifying an oblique plane intersecting a soft tissue represented in the image data and normal to a longitudinal axis of the soft tissue, generating, with the processor, a reformatted image, from the image data, sampled along the oblique plane, tracing a feature of the soft tissue in the reformatted image, and generating, with the processor, a 3-D marking representing the traced feature on a 3-D model. In some implementations, the image data is raw image data.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, devices, and methods described herein, certain illustrative embodiments will be described. Although the embodiments and features described herein are specifically described for use in connection with identifying anatomical landmarks in image data for a patient's knee joint, it will be understood that the approaches disclosed are applicable to other anatomical joints as well. Moreover, the approaches outlined below may be applied to preparing patient-matched medical devices and implants to be used in surgical procedures including, but not limited to, knee, acetabular, spine arthroplasty, cranio-maxillofacial surgical procedures, shoulder arthroplasty, as well as foot, ankle, hand, and other extremity procedures.

The following disclosure provides systems, devices, and methods for identifying anatomical landmarks in image data. Various anatomical landmarks, such as ligament attachment points to the tibia, may be located in the image data using a set of reformatted images that provide a customized view of an anatomical landmark. It will be understood that the set of reformatted images may include two or more reformatted images. A ligament attachment point for which this approach is well-suited is the attachment point between the anterior cruciate ligament (ACL) and the tibia. Any other suitable soft tissue, soft tissue attachment points, or other features of a patient's joint or bone may be identified including, for example, the medial sulcus of the tibia plateau or the lateral sulcus of the tibia plateau as well as attachment points between the medial collateral ligament (MCL) and the tibia, between the posterior cruciate ligament (PCL) and the tibia, between the patellar tendon and the tibia, or any other suitable feature or landmark.

Figure 1:
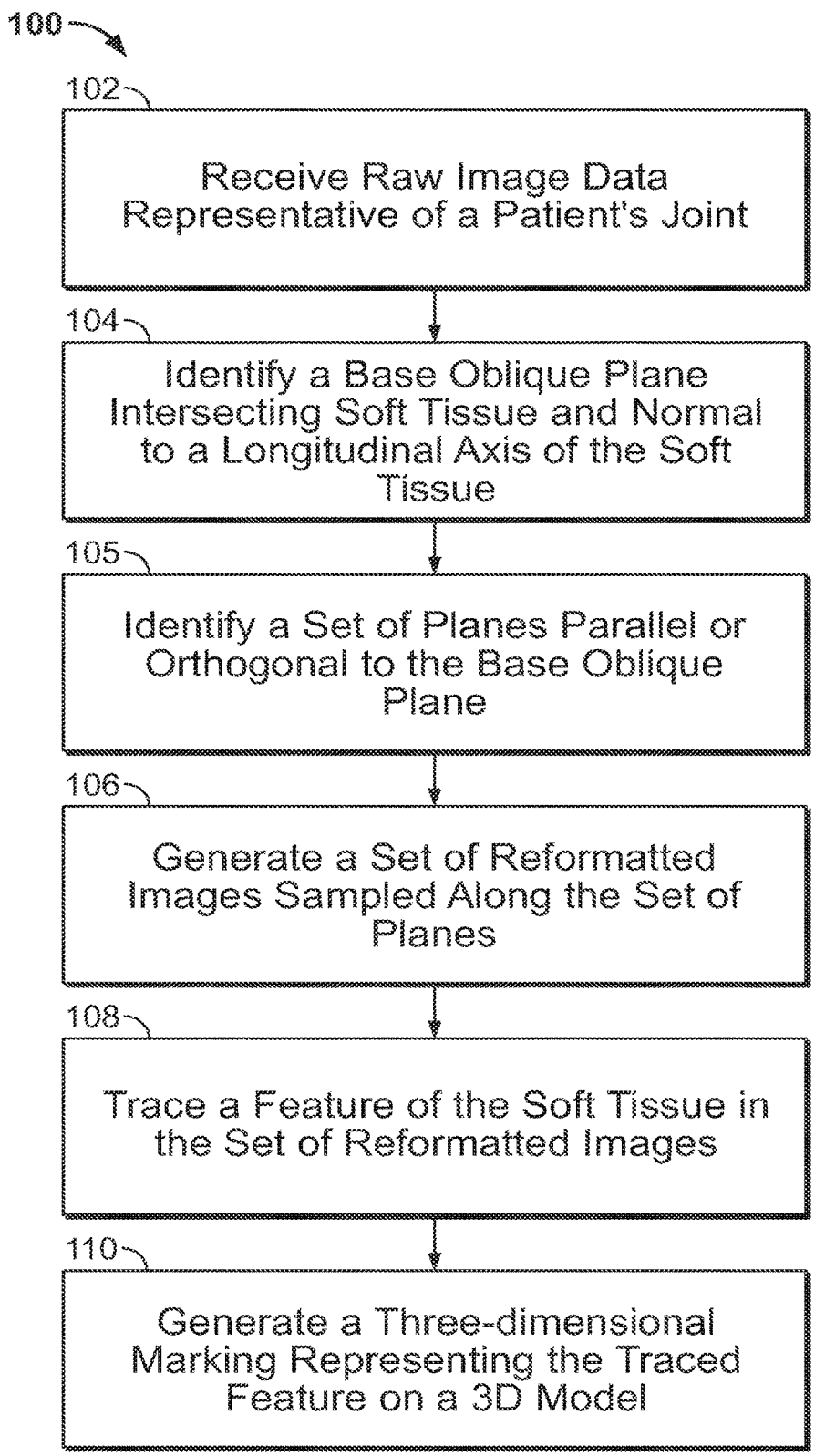
FIG. 1 shows an illustrative flowchart for identifying anatomical landmarks in image data.

FIG. 1 shows a flowchart 100 for identifying anatomical landmarks in image data according to certain embodiments. In step 102, image data representative of a patient's joint is received. The representation of the patient's joint includes soft tissue, such as a ligament, and bone. The soft tissue (e.g. ligament) attaches to the bone at an attachment point. Accurately identifying such an attachment point on a patient's bone provides surgeons with accurate preoperative information about the patient's anatomy and accurate models of a patient's joint for patient-matched instrumentation. The image data received in step 102 can be raw image data. For example, the image data may be received from an imaging machine without significant post-processing. The image data can be obtained using any suitable medical imaging technique including, for example, MRI, CT scan, ultrasound, X-ray, or any other suitable technique or combination thereof. The image data may be topographic image data comprising multiple image slices taken in orthogonal planes. Orthogonal planes for tomographic imaging may include medial-lateral planes (i.e. sagittal planes), anterior-posterior planes (i.e. coronal planes), and transverse planes (i.e. axial planes). These views, however, may not provide the best available view for identifying a particular ligament attachment point. To create a customized set of views that facilitate landmark identification, a user can identify a base oblique plane, oblique to one or more of the orthogonal planes in step 104. The customized set of views may include two or more views. The base oblique plane identified in step 104 is normal to the longitudinal axis of the soft tissue and intersects the soft tissue. Various methods may be used to identify a base oblique plane and are discussed in detail in relation to FIGS. 2-4.

After the base oblique plane is identified, an adjusted set of orthogonal planes that are orthogonal to the base oblique plane is generated in step 105. The adjusted set of orthogonal planes may provide views that effectively rotate the coronal, sagittal, and axial views. An adjusted set of orthogonal planes may be, for example, two or more planes, including the base plane. In step 106, reformatted images are sampled along the adjusted set of orthogonal planes generated in step 105. The reformatted images provide a customized set of views that facilitate identification of soft tissue attachment points on a patient's bone. Additionally, the reformatted images allow the landmark identification to be performed without relying on cross-sectional views of a 3-D model generated from segmentation of the image data. As a result, errors associated with 3-D model generation (e.g. segmentation errors and smoothing errors) are not introduced into the landmark identification process. Thus, accuracy may be increased by limiting the number of processing steps applied to the image data prior to landmark identification.

Figure 5:
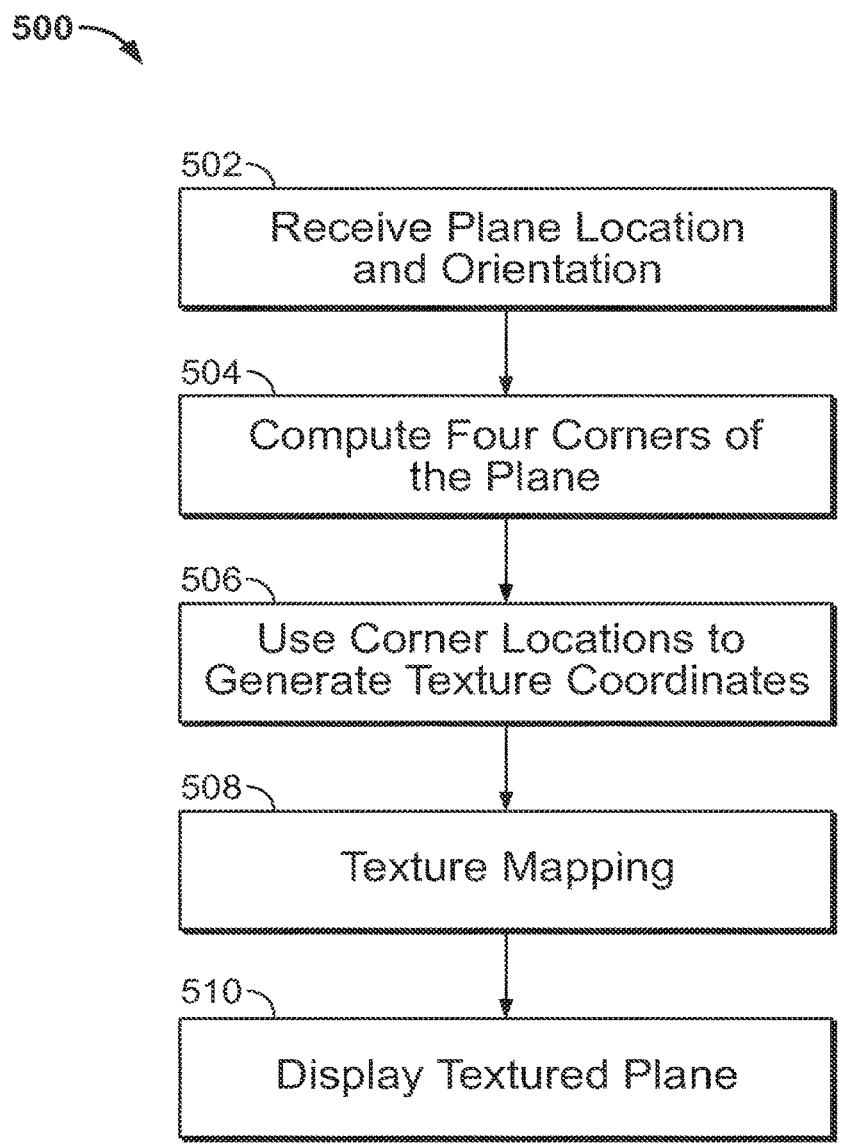
FIG. 5 shows an illustrative flowchart for generating reformatted images sampled along an adjusted set of orthogonal planes.
Figure 6A:
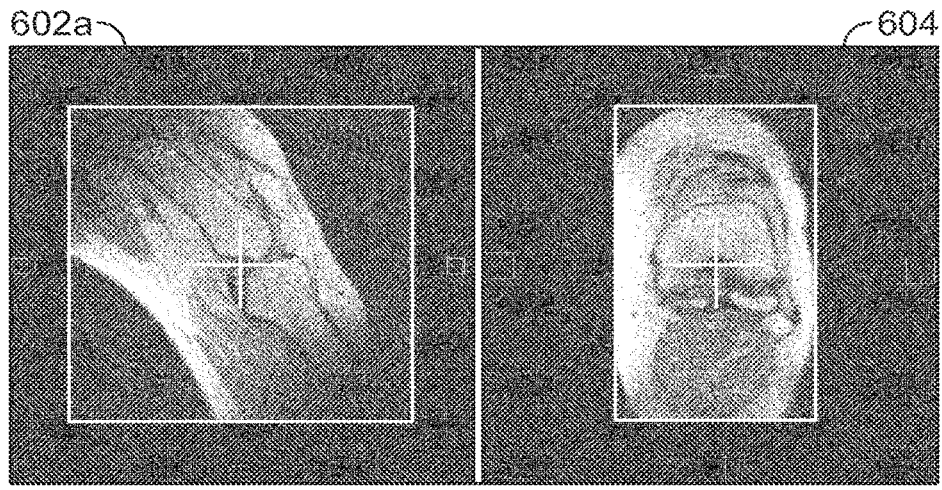
FIGS. 6A and 6B show screenshots of an illustrative graphical user interface displaying reformatted images sampled along the adjusted set of orthogonal planes.
Figure 6B:
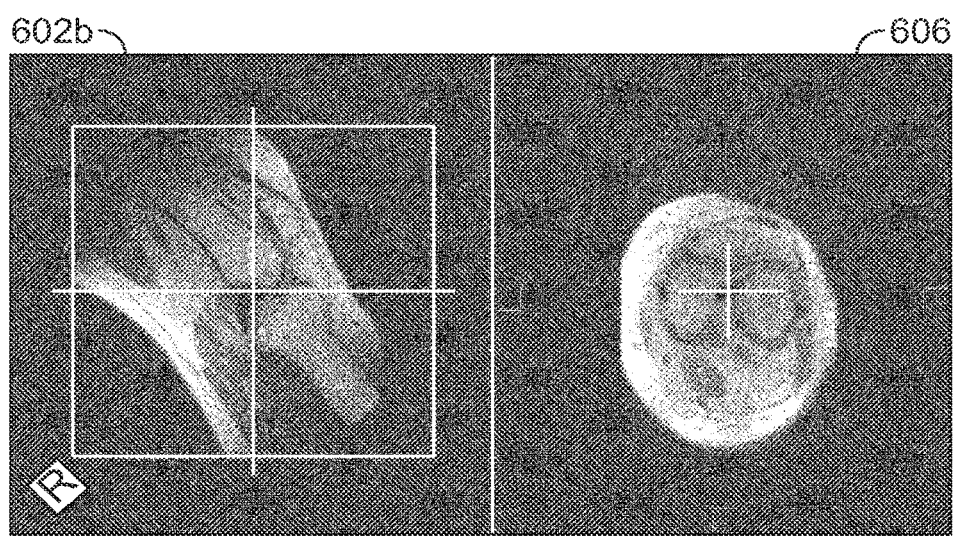
Figure 7:
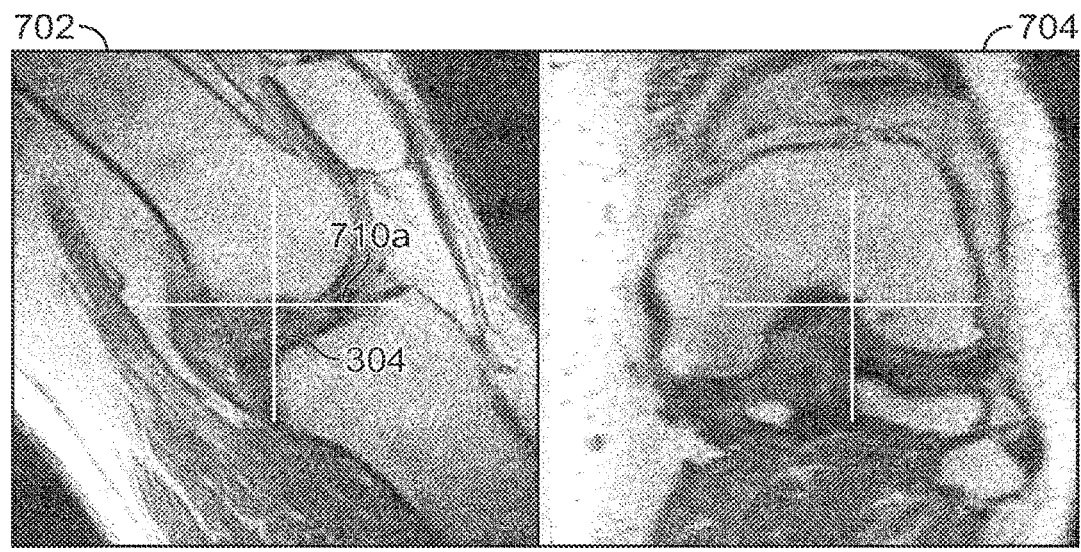
FIG. 7 shows an illustrative graphical user interface for performing a tracing process using multiple views provided by the adjusted set of orthogonal planes.
Figure 7:
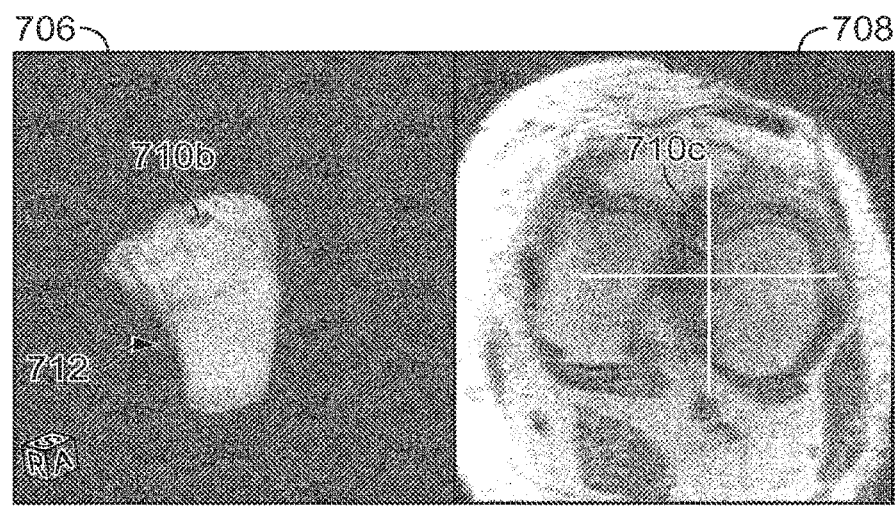

The generation of the reformatted images is further described in relation to FIG. 5 and an illustrative graphical user interface displaying a set of reformatted images is shown in FIGS. 6B and 7. The generation of the reformatted images may be performed by a graphics processing unit (GPU) to reduce processing time, thereby allowing dynamic, "on-the-fly," generation of views more conducive to landmark identification. While a central processing unit (CPU) may also be used, a GPU may be more computationally efficient due to the highly parallel architecture of GPUs. Additionally, generating the reformatted images along the adjusted set of orthogonal planes does not necessarily require the processing capabilities needed to form 3-D models of the joint. Once the reformatted images have been generated, a user traces a feature of the soft tissue in one or more reformatted images in step 108. The process for tracing the soft tissue feature is further described in relation to FIG. 7. Because the user traces this feature from reformatted image data without relying on cross-sectional views of 3-D models generated from segmentation data, segmentation errors and smoothing errors associated with 3-D model generation may be avoided. In step 110, a computer processor uses the tracings to generate a 3-D marking representing the traced feature on a 3-D model. If desired, the 3-D marking can be smoothed as further described in relation to FIG. 8.

Figure 2:
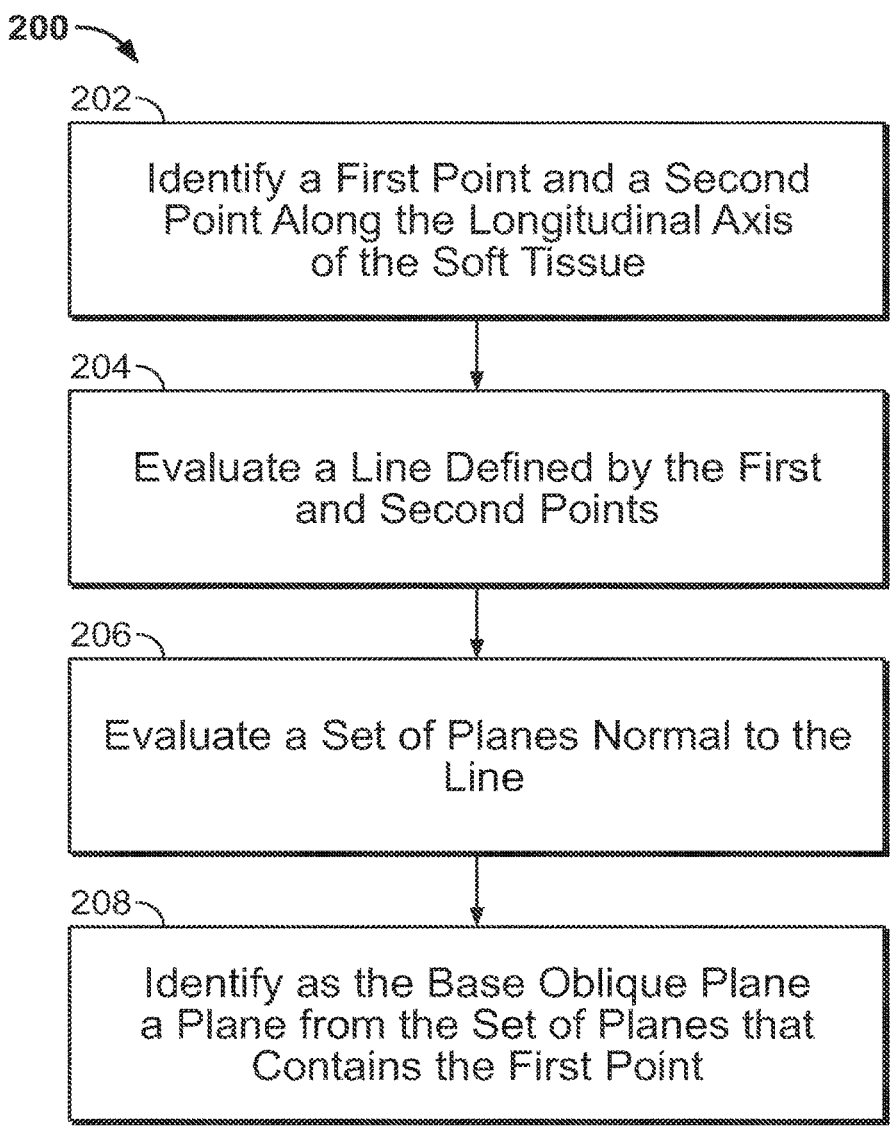
FIG. 2 shows an illustrative flowchart for identifying a base oblique plane.

FIG. 2 shows a flowchart 200 for identifying a base oblique plane according to certain embodiments. For example, the steps of flowchart 200 are related to step 104 of process 100. The steps of process 200 may be performed with reference to the graphical user interface of FIGS. 3 and 4A. In step 202, the user identifies a first point and a second point along the longitudinal axis of the soft tissue. The first and second points may be identified in a first orthogonal slice of raw image data. For identifying ligament attachment points in the knee joint, the orthogonal plane used may be a medial-lateral plane. For example, as shown in FIG. 4A, a first point 410a and a second point 410b are selected in a medial-lateral plane. It may be desirable to locate the first point about where the soft tissue attaches to a patient's bone because the first point may be used later to position a base oblique plane that provides a top view of the attachment point. The second point may be located at about the center of the soft tissue. Such a placement of the first point 410a and the second point 410b is shown in FIG. 4A.

In step 204, the processor evaluates a line defined by the first and second points. For example, as shown in FIG. 4A, line 412 is evaluated based on the location of point 410a and point 410b. The line is then used in step 206 to evaluate a base oblique plane normal to the line. For any given line there is a set of many planes normal to the line and parallel to each other along the length of the line. Therefore, in step 208 one of the planes from the set of planes is identified as the base oblique plane. In some embodiments, the selected base oblique plane is the plane from the set of planes that contains the first point. For example, in FIG. 4B, the selected base oblique plane 424 contains first point 410a. Any other suitable plane from the set of planes that adequately shows the soft tissue attachment point may be selected.

Figure 4A:
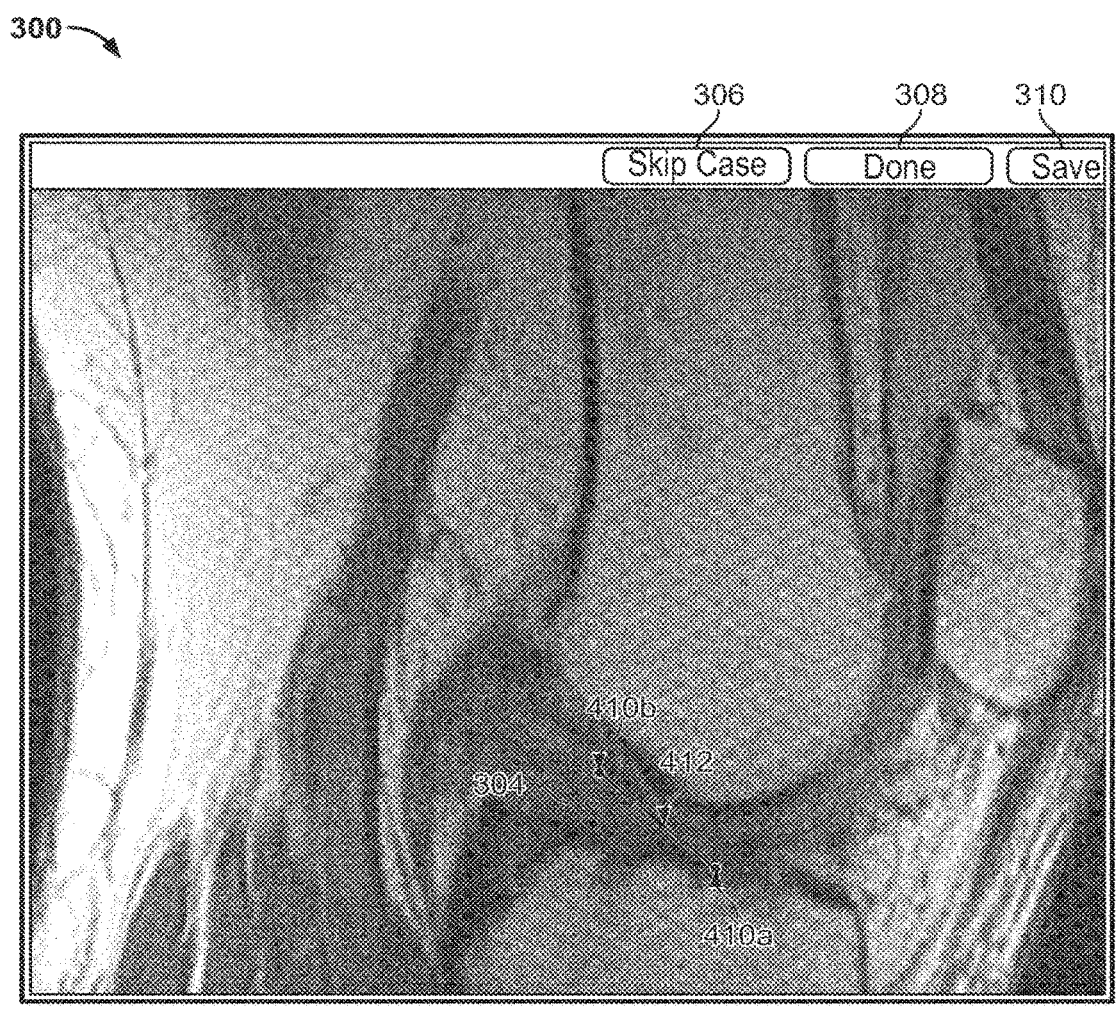
FIG. 4A shows an illustrative graphical user interface for identifying a first point and a second point to identify a line parallel to a longitudinal axis of soft tissue.
Figure 4B:
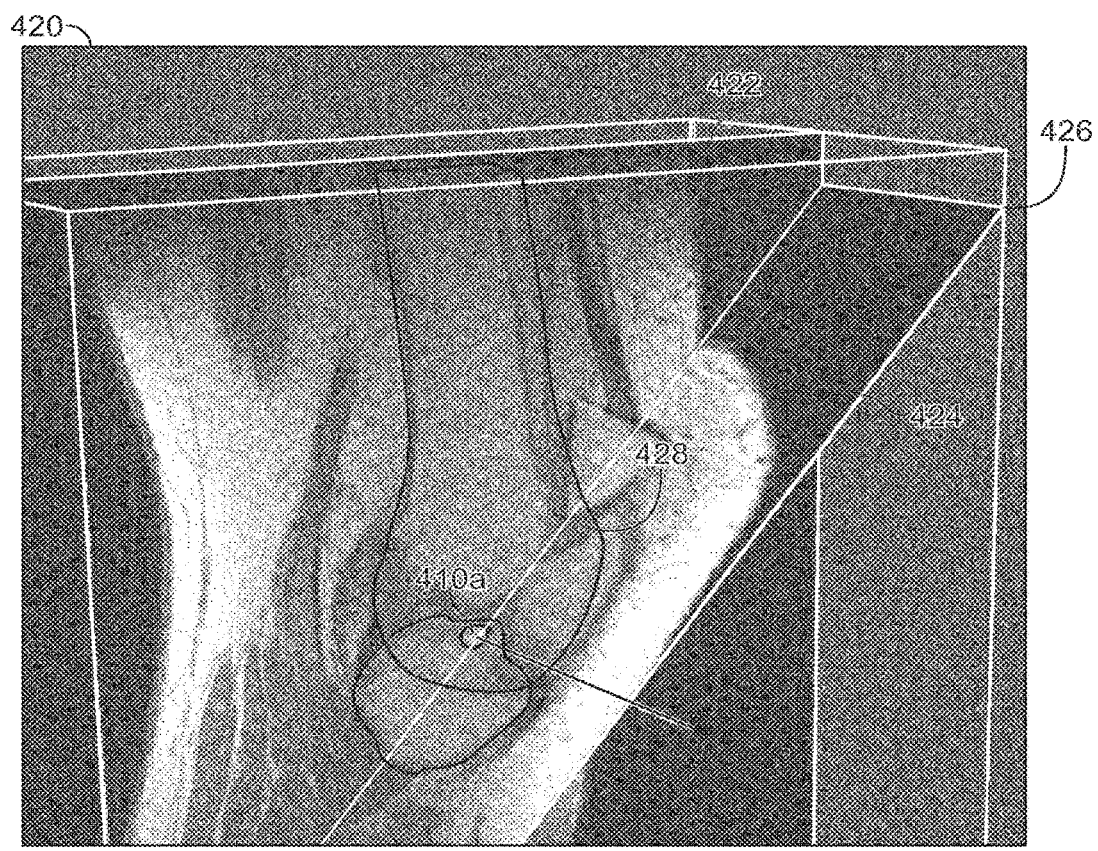
FIG. 4B shows an illustrative preview window that displays a candidate base oblique plane.
Figure 4C:
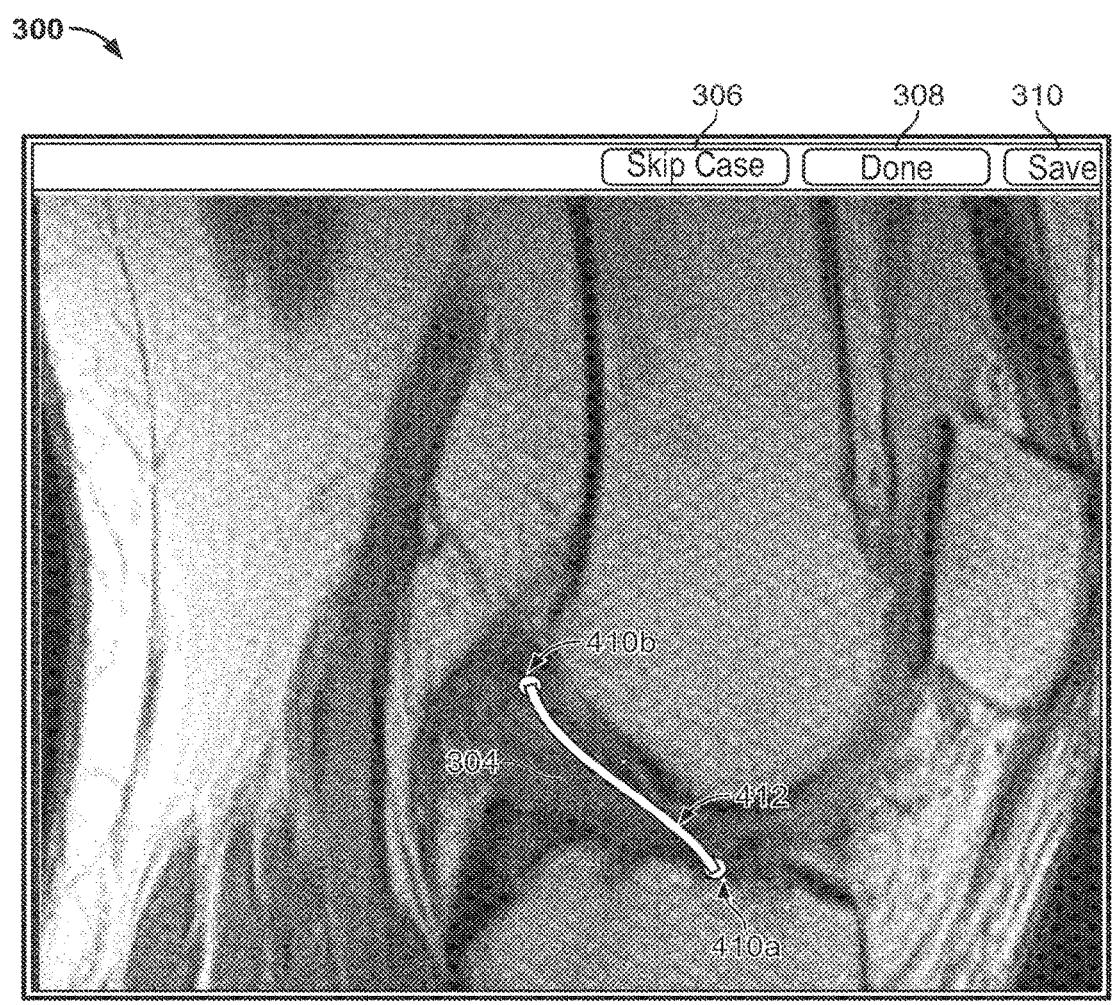
FIG. 4C shows an illustrative graphical user interface for identifying a curve parallel to a longitudinal axis of soft tissue.

FIG. 4C shows a graphical user interface for identifying a curve parallel to a longitudinal axis of soft tissue according to certain embodiments. Because the longitudinal axis of the soft tissue may be curved, a user may be able to draw a curve parallel to the longitudinal axis of the soft tissue instead of a line. When a line is drawn to define the base oblique plane, planes offset from the oblique plane will also be normal to the line. However, when a curve is used to define the base oblique plane, planes offset from that base oblique plane may in some cases not be normal to the curve at the point that the offset plane intersects the curve. Therefore, to better align the adjusted set of orthogonal planes to the curve, multiple base oblique planes may be generated, each base oblique plane being normal to the curve at the point that each plane intersects the curve.

Figure 3:
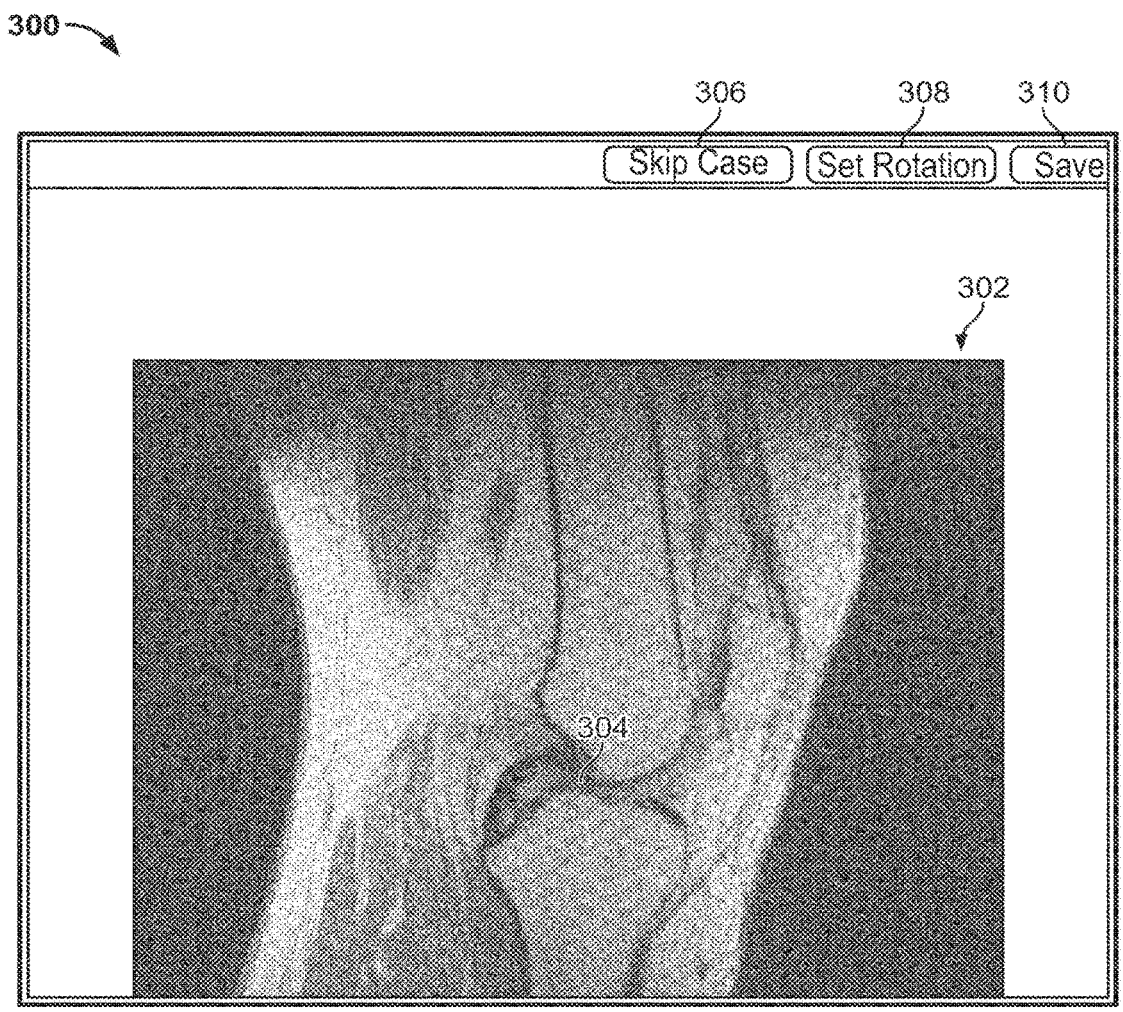
FIG. 3 shows an illustrative graphical user interface for identifying the base oblique plane of FIG. 2.

FIG. 3 shows a graphical user interface 300 for identifying the base oblique plane of FIG. 2 according to certain embodiments. Graphical user interface 300 contains an image window 302, and buttons 306, 308, and 310. The image window displays an orthogonal slice of raw image data. In this example, a medial-lateral slice of a patient's knee joint is shown. Located near the center of the knee joint is a soft tissue 304. The soft tissue shown in the window is the anterior cruciate ligament (ACL). The ACL is a narrow soft tissue structure which attaches to the tibia and the femur. The ACL may not be adequately contained in the orthogonal planes. For better visualization of the ACL and its attachment points, an adjusted set of orthogonal views based on a base oblique plane that intersects the ACL and is normal to the longitudinal axis of the ACL is desired.

Before selecting the first and second points to evaluate the base oblique plane, the image quality may be assessed. Next case button 306 is provided so that a case can be skipped if the image quality is found to be inadequate for analysis. An image can be inadequate for a number of reasons such as low image resolution, poor visibility of the structures to be identified, or absence of segmentation data. The graphical user interface may provide the user with the ability to annotate an inadequate image to note the reason for skipping it. If, however, the image quality is found to be acceptable, the user can press "set rotation" button 308 to initiate the process of identifying an appropriate oblique plane as further described in FIG. 4A. Save button 310 is provided so that users can save their progress at any point during the landmark identification process.

FIG. 4A shows a graphical user interface for identifying a first point and a second point to identify a line parallel to a longitudinal axis of soft tissue according to certain embodiments. After the user has pressed button 308, line 412 and points 410a and 410b appear on the graphical user interface. The user can drag and drop the points 410a and 410b to align line 412 with the longitudinal axis of the soft tissue 304. It may be desirable for line 412 to be placed on the anterior side of the ACL. The first point 410a may be selected to coincide with the attachment point of the ACL, and the second point 410b may be selected to coincide with the midpoint of the ACL although any suitable point along the ACL may be selected. The first point 410a may be used later to select a plane from a set of planes that are normal to line 412. The second point 410b may be used primarily for establishing the slope of line 412. In such an implementation, the exact position of point 410a may be less important than the position of point 410b or the slope of line 412. That is, the direction of the line may be more important than its length.

FIG. 4B shows a preview window 420 that displays a candidate base oblique plane 424 according to certain embodiments. The candidate base oblique plane 424 provides a preview of the base oblique plane that would be generated from the user's current selection of points 410a and 410b. The candidate base oblique plane 424 may be shown in the preview window 420 while the user positions the points 410a and 410b. Such a preview window 420 may aid the user in the process of identifying the first and second points. The candidate base oblique plane is the oblique plane selected from the set of oblique planes normal to line 412 that contains first point 410a.

The preview window 420 also displays a reformatted image on the candidate base oblique plane 424. The user may accept or reject the candidate base oblique plane based on whether the reformatted image provides an adequate view of a ligament attachment point. The reformatted image on the candidate base oblique plane 424 may be generated using a graphics processing unit (GPU) to reduce processing time. Additionally, the preview window 410 displays a 3-D view of both the candidate base oblique plane 424 and an orthogonal slice 422 together so that the user can verify the relative orientation of the candidate base oblique plane. A 3-D model of the patient's bone 428 may also be displayed with the image data to orient the user. If the candidate base oblique plane 424 is found to be inadequate, the user may reposition points 410a and 410b to generate a new candidate base oblique plane 424. If the candidate base oblique plane 424 is found to be acceptable, the user may indicate the acceptance of the plane by clicking a button, and a separate window displaying the reformatted image may appear in the graphical user interface. Example reformatted image windows are shown in FIGS. 6B and 7.

FIG. 5 shows a flowchart 500 for generating reformatted images sampled along the adjusted set of orthogonal planes according to certain embodiments. For example, the steps of flowchart 500 are related to step 106 of process 100. In step 502, the location and orientation of the base oblique plane are received. This location and orientation information defines the base oblique plane. An adjusted set of orthogonal planes may be generated based on the base oblique plane. Each plane in the adjusted set of orthogonal planes is either parallel or orthogonal to the base oblique plane. The oblique planes in the set may be equally spaced and may span the entire volume of the raw image data. Therefore, when the reformatted images are sampled along the oblique planes, the raw image data may be effectively rotated, resulting in a new stack of image slices oriented with the base oblique plane. In the case of the oblique planes generated along a curve, there may be multiple base oblique planes. In such a case, planes orthogonal to each base oblique plane may be generated to provide a set of adjusted orthogonal views that follows the curve. It is also envisioned that the steps here can be performed without identifying a set of orthogonal planes. In such embodiments, a reformatted image may be sampled along the base oblique plane only.

Four corners of the planes in the adjusted set of planes are computed in step 504. The corners of the oblique planes are determined by the intersection of the infinite plane and the bounding volume of the raw image data. For example, as shown in FIG. 4A, candidate base oblique plane 424 has corner 426 at the intersection of the oblique plane and the bounding volume of the raw image data. In step 506, the corners are used to generate texture coordinates for the planes in the adjusted set of orthogonal planes. The texture coordinates are given pixel intensity values for displaying the reformatted image on the oblique plane. Pixel intensity values may represent, for example, radiodensity measurements, attenuation coefficients, or tissue relaxation time such as T1, T2, and proton density. In the texture mapping process of step 508, the pixel intensity values for texture coordinates that do not coincide with points in the raw image data are inferred using interpolation. Possible interpolation methods include nearest-neighbor interpolation, bilinear interpolation, trilinear interpolation, cubic interpolation, and any other suitable technique for interpolation or any combination thereof. One of the differences among the types of interpolation is the assumption of the continuity of the spatial distribution of the pixel values. Linear interpolation, for example, assumes the intensity varies linearly so the unknown value can be determined from its four neighbors as a weighted average. Cubic interpolation, on the other hand, has a higher requirement on the continuity: not only the intensity value but also the first and second order derivatives must be continuous. Cubic interpolation thus requires more neighboring points beyond the immediate four neighbors, but produces results that are smoother. Step 508 may be performed using the graphical processing unit (GPU) or the central processing unit (CPU). Using the GPU instead of the CPU may have performance benefits due to the highly parallel architecture of GPUs. The output of the interpolation step may be a matrix of pixel intensity values, with each value in the matrix corresponding to a generated texture coordinate. The GPU or the CPU sends the output to the display environment in step 510.

FIGS. 6A and 6B show screenshots of a graphical user interface displaying reformatted images sampled along the adjusted set of orthogonal planes. Window 606 shows the reformatted image on the base oblique plane. The image shown in window 606 is the same reformed image that was previewed on candidate base oblique plane 424. Windows 602a and 604 show the corresponding views orthogonal to the base oblique plane. Therefore, windows 602a, 604 and 606 together provide a set of adjusted orthogonal views. Thus, by generating reformatted images along the adjusted set of orthogonal planes, the raw image data is effectively rotated to provide a new stack of image slices oriented with respect to the base oblique plane. The user may be able to advance through the reformatted images in the same way that the user would normally advance through orthogonal slices of the raw image data. Additionally, the user may be provided with a tool bar having toggle buttons that allow different views to be turned on or off.

FIG. 7 shows a graphical user interface for performing a tracing process using multiple views provided by the adjusted set of orthogonal planes according to certain embodiments. Reformatted image window 708 shows an enlarged reformatted image of a patient's knee joint and 2-D marking 710c. 2-D markings may be created by tracing the ACL attachment point in image windows 702, 704, or 708. For example, 2-D marking 710c may be created by tracing the attachment point in image window 708. The 2-D markings may be traced using a cursor controlled by computer mouse. For example, a user may click and hold a mouse button while tracing the ligament attachment point with the cursor to create the 2-D marking. Additionally, a user may advance through reformatted images during tracing. For example, the user may advance through reformatted images normal to the longitudinal axis of the soft tissue beginning just before the ligament attachment point and may stop after the end of the ligament. Advancing through images in this way may facilitate identification of the end of a ligament, and therefore the ligament attachment point, because there may be a sharp change in the grayscale of the cross-sections as the end of the ligament is passed. Alternatively, a user may start just before the starting point of a ligament and advance through reformatted images until the end of the ligament is reached or just passed. Advancing in this way may allow user to identify attachment points on both ends of the ligament. For example, advancing from the start of the ACL to its end may facilitate identification of both the attachment point to the femur and the attachment point to the tibia.

As the user advances through reformatted images, the user may outline the cross-sections of a ligament in any of the adjusted orthogonal planes. Additionally, a user may also be provided with the ability to erase all or a part of a 2-D marking made in any view. It may be desirable to advance through 8 to 10 reformatted images during tracing to adequately mark an attachment point. As the user traces the attachment point in the cross-sections, a matrix representing the tracing data may be generated. For example, the data representing the points selected during tracing may be stored in a binary map. This tracing data may be used to generate a 3-D marking as discussed further in relation to FIG. 8.

The graphical user interface of FIG. 7 also contains surface model window 706 which displays a 3-D surface model 712 representing a patient's tibia. The 3-D surface model may help orient the user to the patient's anatomy during tracing. The 3-D surface model may be created prior to tracing based on segmentation of the raw image data. The same 2-D marking traced in the adjusted orthogonal planes is displayed as marking 710b on the 3-D surface model 712. Thus, the graphical user interface may facilitate creation of 2-D markings representing the ligament attachment point.

Figure 8:
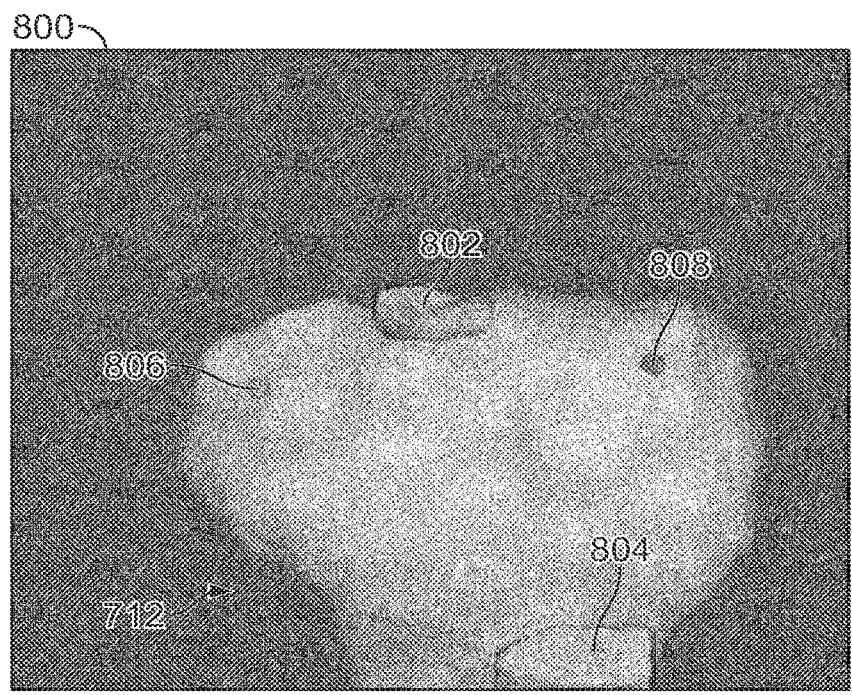
FIG. 8 shows illustrative 3-D markings generated from tracing data.

FIG. 8 shows 3-D markings generated from tracing data according to certain embodiments. The 3-D markings may be generated using the 2-D markings created in the tracing process described in FIG. 7. For example, 3-D marking 802, which represents the ACL attachment point to the tibia, is generated from 2-D markings 710a and 710c. In certain implementations, 3-D marking 802 may be generated from the tracing data using the marching cubes algorithm. 3-D marking 804, which represents the patellar tendon attachment point to the anterior side of the tibia, can be created by a similar process as that used to create 3-D marking 802. Alternatively, point markings 806 and 808 may each be created from the identification of a single landmark point in one or more of the adjusted orthogonal planes. The point marking 806 is selected to correspond to the medial sulcus of the tibia plateau and point marking 808 is selected to correspond to the lateral sulcus of the tibia plateau. The point markings are selected to correspond to the lowest points on the tibia condyles. Additionally, smoothing may be performed on the surface model or on the tracing data before generation of the surface model. Such smoothing may be performed for processing efficiency because smoothed 3-D markings may not require subsequent smoothing when imported into a computer aided design (CAD) environment. Thus, the tracing process described in relation to FIG. 7 may be used to generate 3-D markings representing anatomical landmarks, such as ligament attachment points.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in knee arthroplasty systems, may be applied to systems, devices, and methods to be used in other surgical procedures including, but not limited to, acetabular, spine arthroplasty, craniomaxillofacial surgical procedures, shoulder arthroplasty, as well as foot, ankle, hand, and extremities procedures.

EXAMPLE EMBODIMENTS

A1. A method for locating anatomical landmarks in image data, comprising:
receiving, at a processor, image data representative of a patient's joint;
identifying an oblique plane intersecting a soft tissue represented in the image data and normal to a longitudinal axis of the soft tissue;

identifying, with the processor, a set of planes comprising the oblique plane and at least one other plane parallel or orthogonal to the oblique plane;

generating, with the processor, a set of reformatted images, from the image data, sampled along the set of planes;

tracing a feature of the soft tissue in the set of reformatted images; and generating, with the processor, a 3-D marking representing the traced feature on a 3-D model.

A2. The method of embodiment A1, wherein tracing the feature comprises tracing the feature in two or more reformatted images parallel to the oblique plane.

A3. The method of embodiment A1 or A2, wherein tracing the feature comprises:

displaying a first reformatted image on a screen; and displaying a second reformatted image on the screen, wherein the second reformatted image is parallel to and offset from the first reformatted image.

A4. The method of any of embodiments A1-A3, wherein tracing the feature comprises outlining a cross-section of the feature in a reformatted image from the set of reformatted images.

A5. The method of any of embodiments A1-A4, wherein tracing the feature comprises storing data representing the tracing in a matrix.

A6. The method of any of embodiments A1-A5, wherein generating the set of reformatted images comprises rotating the image data.

A7. The method of any of embodiments A1-A6, wherein identifying the oblique plane comprises:

identifying a first point and a second point along the longitudinal axis of the soft tissue;

evaluating, with the processor, a line defined by the first and second points; and evaluating, with the processor, a plane normal to the line.

A8. The method of any of embodiments A1-A7, wherein the first point is located about where the soft tissue attaches to a patient's bone.

A9. The method of any of embodiments A1-A8, wherein the second point is located at about the center of the soft tissue.

A10. The method of any of embodiments A1-A7, wherein the first point is located at about the start of the soft tissue and the second point is located at about the end of the soft tissue.

A11. The method of any of embodiments A1-A10, wherein the longitudinal axis of the soft tissue is curved.

A12. The method of embodiment A11, wherein identifying the oblique plane comprises:

drawing a curve substantially parallel to the longitudinal axis of the tissue; and evaluating, with the processor, an oblique plane normal to the curve at the point where the oblique plane intersects the curve.

A13. The method of embodiment A11 or A12, wherein a plurality of reformatted images is generated, each reformatted image being normal to the curve at the point where each reformatted image intersects the curve.

A14. The method of any of embodiments A1-A13, wherein generating the 3-D marking comprises generating a 3-D surface model from the matrix.

A15. The method of any of embodiments A1-A14, further comprising smoothing the 3-D marking.

A16. The method of any of embodiments A1-A15, wherein the 3-D model is a model of a patient's bone.

A17. The method of any of embodiments A1-A16, wherein the 3-D model is a model of a patient's tibia.

A18. The method of any of embodiments A1-A17 wherein the 3-D model is displayed with the image data to orient a user.

A19. The method of any of embodiments A1-A18, wherein generating the set of reformatted images comprises:

identifying, with the processor, four corners of the oblique plane;

generating, with the processor, texture coordinates using the corner locations; and interpolating, with the processor, pixel intensities for the texture coordinates using the image data.

A20. The method of any of embodiments A1-A19, wherein the soft tissue is an ACL, a MCL, a PCL, or a patellar tendon of a patient.

B1. A system for locating anatomical landmarks in image data, comprising:

means for receiving image data representative of a patient's joint;

means for identifying an oblique plane intersecting a soft tissue represented in the image data and normal to a longitudinal axis of the soft tissue;

means for identifying a set of planes parallel or orthogonal to the oblique plane;

means for generating a set of reformatted images, from the image data, sampled along the set of planes;

means for tracing a feature of the soft tissue in the set of reformatted images; and means for generating a 3-D marking representing the traced feature on a 3-D model.

B2. The system of embodiment B1, wherein the means for tracing the feature comprises means for tracing the feature in two or more reformatted images parallel to the oblique plane.

B3. The system of embodiment B1 or B2, wherein the means for tracing the feature comprises means for advancing through parallel reformatted images selected from the set of reformatted images.

B4. The system of any of embodiments B1-B3, wherein the means for tracing the feature comprises means for outlining a cross-section of the feature in a reformatted image from the set of reformatted images.

B5. The system of any of embodiments B1-B4, wherein the means for tracing the feature comprises means for storing data representing the tracing in a matrix.

B6. The system of any of embodiments B1-B5, wherein the means for generating the set of reformatted images comprises means for rotating the image data.

B7. The system of any of embodiments B1-B6, wherein the means for identifying the oblique plane comprises:

means for identifying a first point and a second point along the longitudinal axis of the soft tissue;

means for evaluating a line defined by the first and second points; and means for evaluating a plane normal to the line.

B8. The system of any of embodiments B1-B7, wherein the first point is located about where the soft tissue attaches to a patient's bone.

B9. The system of any of embodiments B1-B8, wherein the second point is located at about the center of the soft tissue.

B10. The system of any of embodiments B1-B7, wherein the first point is located at about the start of the soft tissue and the second point is located at about the end of the soft tissue.

B11. The system of any of embodiments B1-B10, wherein the longitudinal axis of the soft tissue is curved.

B12. The system of embodiment B11, wherein the means for identifying the oblique plane comprises:

means for drawing a curve substantially parallel to the longitudinal axis of the tissue; and means for evaluating an oblique plane normal to the curve at the point where the oblique plane intersects the curve.

B13. The system of embodiment B11 or B12, wherein a plurality of reformatted images is generated, each reformatted image being normal to the curve at the point where each reformatted image intersects the curve.

B14. The system of any of embodiments B1-B13, wherein the means for generating the 3-D marking comprises means for generating a 3-D surface model from the matrix.

B15. The system of any of embodiments B1-B14, further comprising means for smoothing the 3-D marking.

B16. The system of any of embodiments B1-B15, wherein the 3-D model is a model of a patient's bone.

B17. The system of any of embodiments B1-B16, wherein the 3-D model is a model of a patient's tibia.

B18. The system of any of embodiments B1-B17 wherein the 3-D model is displayed with the image data to orient a user.

B19. The system of any of embodiments B1-B18, wherein the means for generating the set of reformatted images comprises:

means for computing four corners of the oblique plane;

means for generating texture coordinates using the corner locations; and means for interpolating pixel intensities for the texture coordinates using the image data.

B20. The system of any of embodiments B1-B19, wherein the soft tissue is an ACL, a MCL, a PCL, or a patellar tendon of a patient.

C1. A method for locating anatomical landmarks in image data, comprising:

receiving, at a processor, image data representative of a patient's joint;

identifying an oblique plane intersecting a soft tissue represented in the image data and normal to a longitudinal axis of the soft tissue;

generating, with the processor, a reformatted image, from the image data, sampled along the oblique plane;

tracing a feature of the soft tissue in the reformatted image; and generating, with the processor, a 3-D marking representing the traced feature on a 3-D model.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A system for locating anatomical landmarks in image data, comprising:

a device configured to receive image data representative of a patient's joint;

one or more graphical user interface units configured to:

receive user inputs identifying a first point and a second point along a portion of soft tissue of the patient represented in the image data representative of the patient's joint;

receive user inputs tracing a feature of the portion of soft tissue of the patient having a longitudinal axis;

one or more processors coupled to the device configured to receive image data representative of a patient's joint and the one or more graphical user interface units configured to:

identify one of a line or a curve that connects the first point and the second point along a portion of soft tissue of the patient;

identify a set of planes comprising (i) an oblique plane intersecting a normal to the line or the curve and (ii) at least one other plane parallel to the oblique plane;

generate, using the image data representative of the patient's joint, a set of reformatted images;

generate a 3-D model representative of the patient's joint using the set of reformatted images;

generate a 3-D marking representing the traced feature of the portion of soft tissue of the patient on the 3-D model representative of the patient's joint; and one or more screens coupled to the one or more graphical user interface units and the one or more processors configured to display one or more of the image data representative of the patient's joint, the first point and the second point along the portion of soft tissue of the patient represented in the image data representative of the patient's joint, the traced feature of the portion of soft tissue of the patient, the oblique plane, the 3-D model representative of the patient's joint, one or more reformatted images from the set of reformatted images, and the 3-D marking representing the traced feature of the portion of soft tissue of the patient.

2. The system of claim 1, wherein the image data representative of the patient's joint comprises image slices taken in parallel image planes selected from one of sagittal planes, coronal planes, or axial planes of the patient.

3. The system of claim 2, wherein the oblique plane is parallel to the parallel image planes.

4. The system of claim 1, wherein receiving user inputs tracing the feature of the portion of soft tissue of the patient comprises receiving user inputs tracing the feature in two or more reformatted images from the set of reformatted images.

5. The system of claim 1, wherein receiving user inputs tracing the feature of the portion of soft tissue of the patient comprises:

displaying on the one or more graphical user interface units a first reformatted image from the set of reformatted images; and displaying on the one or more graphical user interface units a second reformatted image from the set of reformatted images, wherein the second reformatted image is parallel to and offset from the first reformatted image.

6. The system of claim 1, wherein the 3-D model of the patient's joint is generated using the image data of the patient's joint prior to tracing the feature of the portion of soft tissue of the patient.

7. The system of claim 1, wherein receiving user inputs tracing the feature of the soft tissue of the patient comprises storing data representing the tracing in a matrix.

8. The system of claim 1, wherein receiving user inputs tracing the feature of the soft tissue of the patient comprises outlining a cross-section of the feature of the soft tissue of the patient one or more reformatted images from the set of reformatted images.

9. The system of claim 1, wherein generating the set of reformatted images comprises sampling the image data representative of the patient's joint along the oblique plane.

10. The system of claim 1, wherein the one or more graphical user interface units further comprise one or more pointing devices, including a mouse.

11. The system of claim 1, wherein the first point along the portion of soft tissue of the patient is an attachment point of the soft tissue of the patient to the patient's bone and the second point along the portion of soft tissue of the patient is a midpoint of the soft tissue of the patient.

12. The system of claim 1, wherein the soft tissue of the patient is a patellar tendon of a patient.

13. A system for locating anatomical landmarks in image data, comprising:
   a device configured to generate image data representative of a patient's joint;
   one or more graphical user interface units configured to:
      receive user inputs identifying a first point and a second point along a portion of soft tissue of the patient represented in the image data representative of the patient's joint;
      receive user inputs tracing a feature of the portion of soft tissue of the patient having a longitudinal axis that is curved;
   one or more processors coupled to the device configured to receive image data representative of a patient's joint and the one or more graphical user interface units configured to:
      identify one of a line or a curve that connects the first point and the second point along a portion of soft tissue of the patient;
      identify a set of planes comprising (i) an oblique plane intersecting a normal to the line or the curve and (ii) at least one other plane parallel to the oblique plane;
      generate, using the image data representative of the patient's joint, a set of reformatted images;
      generate a 3-D model representative of the patient's joint using the set of reformatted images;
      generate a 3-D marking representing the traced feature of the portion of soft tissue of the patient on the 3-D model representative of the patient's joint; and
   one or more screens coupled to the one or more graphical user interface units and the one or more processors configured to display one or more of the image data representative of the patient's joint, the first point and the second point along the portion of soft tissue of the patient represented in the image data representative of the patient's joint, the traced feature of the portion of soft tissue of the patient, the oblique plane, the 3-D model representative of the patient's joint, one or more reformatted images from the set of reformatted images, and the 3-D marking representing the traced feature of the portion of soft tissue of the patient.

14. The system of claim 13, wherein identifying the oblique plane comprises:
   receiving, at the one or more graphical user interfaces, a user input identifying a curve substantially parallel to the longitudinal axis of the portion of soft tissue of the patient; and
   evaluating, using the one or more processors, an oblique plane normal to the curve at the point where the oblique plane intersects the curve.

15. The system of claim 13, wherein the set of reformatted images is normal to the curve at the point where each reformatted image intersects the curve.

16. A system for locating anatomical landmarks in image data, comprising:
   a device configured to receive image data representative of a patient's joint;
   one or more graphical user interface units configured to:
      receive user inputs identifying a first point and a second point along a portion of soft tissue of the patient represented in the image data representative of the patient's joint;
      receive user inputs tracing a feature of the portion of soft tissue of the patient having a longitudinal axis;
   one or more processors coupled to the device configured to receive image data representative of a patient's joint and the one or more graphical user interface units configured to:
      identify one of a line or a curve that connects the first point and the second point along a portion of soft tissue of the patient;
      identify a set of planes comprising (i) an oblique plane intersecting a normal to the line or the curve and (ii) at least one other plane parallel to the oblique plane;
      generate, using the image data representative of the patient's joint, a set of reformatted images by:
         receiving the location and orientation of the oblique plane;
         generating a set of oblique planes parallel or orthogonal to the oblique plane;
         sampling the image data representative of the patient's joint along the set of oblique planes;
         computing the corners of the set of oblique planes by determining the intersection of each of the oblique planes in the set of oblique planes with the image data representative of the patient's joint;
         generating texture coordinates using the corners of the set of the oblique planes;
         assigning pixel intensity values to the texture coordinates; and
         interpolating pixel intensity values for texture coordinates that do not coincide with points in the image data representative of the patient's joint;
      generate a 3-D model representative of the patient's joint using the set of reformatted images;
      generate a 3-D marking representing the traced feature of the portion of soft tissue of the patient on the 3-D model representative of the patient's joint; and
   one or more screens coupled to the one or more graphical user interface units and the one or more processors configured to display one or more of the image data representative of the patient's joint, the first point and the second point along the portion of soft tissue of the patient represented in the image data representative of the patient's joint, the traced feature of the portion of soft tissue of the patient, the oblique plane, the 3-D model representative of the patient's joint, one or more reformatted images from the set of reformatted images, and the 3-D marking representing the traced feature of the portion of soft tissue of the patient.

17. The system of claim 16, wherein the set of oblique planes span the entire volume of the image data representative of the patient's joint.

18. The system of claim 16, wherein the set of oblique planes are equally spaced.

19. The system of claim 16, wherein the pixel intensity values represent radiodensity measurements, attenuation coefficients, tissue relaxation time, or proton density.

20. The system of claim 16, wherein the interpolation is achieved using nearest-neighbor interpolation, bilinear interpolation, trilinear interpolation, cubic interpolation, or any combination thereof.

* * * * *